United States Patent [19]

Bielecki

[11] Patent Number: 5,533,305
[45] Date of Patent: Jul. 9, 1996

[54] TREATMENT BOOTH FOR INFECTIOUS PATIENTS

[75] Inventor: James J. Bielecki, Bloomingdale, N.J.

[73] Assignee: Mark Solutions, Inc., Maywood, N.J.

[21] Appl. No.: 298,045

[22] Filed: Aug. 30, 1994

[51] Int. Cl.⁶ .................................................. E04H 1/12
[52] U.S. Cl. .................. 52/79.1; 52/480; 52/664; 52/668; 297/343; 55/482; 55/483; 55/503; 454/158; 454/187
[58] Field of Search ........................... 52/79.1, 480, 664, 52/666, 668, 348; 297/14, 343, 180.14, 395; 454/158, 187; 55/482, 483, 503, 506, 508

[56] References Cited

U.S. PATENT DOCUMENTS

| | | | |
|---|---|---|---|
| 1,024,001 | 4/1912 | Forsyth | 52/668 |
| 1,802,607 | 4/1931 | Krause | 297/343 |
| 2,275,349 | 3/1942 | Collender | 52/664 X |
| 3,252,580 | 5/1966 | Getzin | 55/503 X |
| 3,511,162 | 5/1970 | Truhan | 128/205.26 X |
| 3,517,468 | 6/1970 | Woods | 52/79.1 |
| 3,601,031 | 8/1971 | Abel et al. | 454/187 |
| 3,745,991 | 7/1973 | Gauthier et al. | 128/2 R |
| 3,966,442 | 6/1976 | Waters | 55/482 X |
| 4,337,708 | 7/1982 | Peterson | 52/666 X |
| 4,344,784 | 8/1982 | Deckas et al. | 55/483 X |
| 4,409,889 | 10/1983 | Burleson | 52/79.1 X |
| 4,630,530 | 12/1986 | Eckstrom et al. | 454/158 X |
| 4,838,575 | 6/1989 | Livingston | 297/395 X |
| 4,987,706 | 1/1991 | Hughes et al. | 52/79.1 X |
| 5,160,517 | 11/1992 | Hicks et al. | 297/180.14 X |
| 5,233,975 | 8/1993 | Choate | 128/200.14 |
| 5,372,126 | 12/1994 | Blau | 128/205.12 X |

FOREIGN PATENT DOCUMENTS

| | | | |
|---|---|---|---|
| 2576624 | 8/1986 | France | 52/79.1 |
| 2125180 | 12/1972 | Germany | 52/79.1 |
| 2-49862 | 2/1990 | Japan | 52/79.1 |

Primary Examiner—Carl D. Friedman
Assistant Examiner—Laura A. Saladino
Attorney, Agent, or Firm—Lerner, David, Littenberg

[57] ABSTRACT

Treatment booth provides patient isolation for sputum induction and aerosolized treatment. The booth is provided with a seat assembly to enable a patient to comfortably recline in a number of positions. Hazardous microbial airborne particles within the booth are filtered using a removable HEPA filter and U.V. germicidal radiation lamps supported by a rigid floor assembly constructed from a grid of interconnected longitudinal and transverse members.

42 Claims, 14 Drawing Sheets

TREATMENT BOOTH FOR INFECTIOUS PATIENTS

BACKGROUND OF THE INVENTION

The present invention relates in general to a treatment booth for infectious patients, and more particularly, to a treatment isolation booth for sputum induction or aerosolized treatments such as pentamidine and the like.

Treatment booths have been widely used in various applications such as to protect against hazardous microbial airborne particles which include the *tuberculosis bacilli* and other infectious respiratory organisms at hospitals and the like. Tuberculosis, in particular, has become a nationwide dilemma. Recent outbreaks of new drug resistant strains have surfaced in many locations. It is estimated that over one million persons are infected with HIV which is a contributing factor to the current tuberculosis epidemic. Recent reports state that some ten million Americans are currently infected with tuberculosis.

Isolation or negative pressure treatment booths have been found to be the most effective in handling infectious patients since they restrict the patient, while at the same time, prevent the spread of microbial airborne particles which include infectious respiratory organisms. To this end, there is known a treatment booth available from Mark Solutions, Inc. of Maywood, N.J. The treatment booth is provided with a number of features which provide contamination control designed for safety for staff and patients during treatment and diagnostic procedures. For example, a completely self-contained negative-pressure environment is provided having a range of 260–470 complete air changes per hour. High filtration with High Efficiency Particulate Air (HEPA) filters and germicidal irradiation with fully shielded ultraviolet lighting treats discharged air to the surrounding environment. As such, the treatment booth is safe for sputum induction procedures as well as being safe for aerosolized drug treatment by not allowing leakage of the therapy agents to the surrounding area. Despite the success of the treatment booth, there is the desire for certain design improvements, hence, the need for the present invention.

SUMMARY OF THE INVENTION

One object of the present invention is to provide a treatment booth in the nature of an improved self contained sputum induction/aerosol treatment booth.

Another object of the present invention is to provide a treatment booth which minimizes the risk of spreading infectious diseases to the physician, staff and all other patients in a health care facility.

Another object of the present invention is to provide a treatment booth containing HEPA filters for performing sputum induction procedures in a negative pressure environment.

Another object of the present invention is to provide a treatment booth which provides contamination control and safety for staff and patients during treatment and diagnostic procedures.

In accordance with one embodiment of the present invention there is described a treatment booth for confining a person having a communicable disease in an isolated environment, the booth comprising a housing having a floor for confining a person therein, a frame supporting the floor including a plurality of elongated first members and a plurality of elongated second members arranged in a grid, the first members having a plurality of spaced apart openings for receiving the second members therein wherein the upper surface of the first members is substantially flush with the upper surface of the second members for support of the floor thereacross, access means within the housing for ingress and egress of a person into and out of the interior of the housing, and treatment means within the housing for treating the contaminated environment within the interior of the housing resulting from the presence of a person therein having a communicable disease.

In accordance with another embodiment of the present invention there is described a treatment booth for confining a person having a communicable disease in an isolated environment, the booth comprising a housing having a floor for confining a person therein, a frame supporting the floor including a plurality of elongated U-shaped longitudinal members and a plurality of elongated U-shaped transverse members arranged in a grid, the longitudinal members having a plurality of spaced apart openings for receiving the transverse members therein, the openings comprising a rectangular opening and a pair of notches on either side of the rectangular opening, the transverse members having one portion received within the rectangular opening and another portion received within the notches wherein the upper surface of the longitudinal members is substantially flush with the upper surface of the transverse members for support of the floor thereacross, access means within the housing for ingress and egress of a person into and out of the interior of the housing, and treatment means within the housing for treating the contaminated environment within the interior of the housing resulting from the presence of a person therein having a communicable disease.

In accordance with another embodiment of the present invention there is described a treatment booth for confining a person having a communicable disease in an isolated environment, the booth comprising a housing for confining a person therein, access means within the housing for ingress and egress of a person into and out of the interior of the housing, and an air filter assembly within the housing for treating the contaminated environment therein resulting from the presence of a person having a communicable disease, the air filter assembly comprising a primary filter for treatment of contaminated air within the housing, a first frame overlying one surface of the primary filter having an opening in communication therewith for the flow of contaminated air therethrough, a prefilter overlying the opening within the first frame, and a second frame overlying one surface of the prefilter having an opening in communication therewith for the flow of contaminated air therethrough, the second frame having a portion releasably secured by a portion of the first frame whereby said primary filter and the prefilter are accessible for replacement upon removal of the first and second frames.

In accordance with another embodiment of the present invention there is described a treatment booth for confining a person having a communicable disease in an isolated environment, the booth comprising a housing for confining a person therein, access means within the housing for ingress and egress of a person into and out of the interior of the housing, and an air filter assembly within the housing for treating the contaminated environment therein resulting from the presence of a person having a communicable disease, the air filter assembly comprising a primary filter for treatment of contaminated air within the housing, a first frame overlying one surface of the primary filter having an opening in communication therewith for the flow of contaminated air therethrough, a prefilter overlying the opening within the first frame, and a second frame overlying one surface of the prefilter having an opening in communication therewith for the flow of contaminated air therethrough, the second frame having one portion releasably secured by a U-shaped member extending outwardly along one side of the first frame and another portion engaging a portion of the housing for releasably securing the second frame thereat, whereby the primary filter and the prefilter are accessible for replacement upon removal of the first and second frames, means within the housing for drawing contaminated air from within the housing through both the prefilter and the primary filter, and discharging clean filtered air to the surrounding environment outside the housing.

In accordance with another embodiment of the present invention there is described a treatment booth for confining a person having a communicable disease in an isolated environment, the booth comprising a housing for confining a person therein, a seat within the housing for supporting a person having a position adjustable backrest, a locking assembly for releasably locking the backrest in a plurality of positions, the locking assembly including a tracking guide attached to the backrest and a locking bracket releasably engaging the tracking guide for securing the backrest in the plurality of positions.

In accordance with another embodiment of the present invention there is described a treatment booth for confining a person having a communicable disease in an isolated environment, the booth comprising a housing for confining a person therein, a seat within the housing for supporting a person having a position adjustable backrest, a locking assembly for releasably locking the backrest in a plurality of positions, the locking assembly including a tracking guide attached to the backrest comprising a U-shaped member having a rod for securing the backrest in one of the plurality of positions, and a locking bracket releasably engaging the tracking guide for securing the backrest in the plurality of positions, the locking bracket including an outer member, an inner member received within the outer member forming a channel therebetween receiving the rod of the tracking guide, a pivotable member overlying the channel, the pivotable member having a plurality of openings for receiving the rod for securing the backrest in one of the plurality of positions and a flange overlying a portion of the inner member, and securing means for releasably securing the flange to the portion of the inner member.

In accordance with another embodiment of the present invention there is described a treatment booth for confining a person having a communicable disease in an isolated environment, the booth comprising a housing having a floor for confining a person therein; a frame supporting the floor including a plurality of elongated U-shaped longitudinal members and a plurality of elongated U-shaped transverse members arranged in a grid, the longitudinal members having a plurality of spaced apart openings for receiving the transverse members therein, the openings comprising a rectangular opening and a pair of notches on either side of the rectangular opening, the transverse members having one portion received within the rectangular opening and another portion received within the notches wherein the upper surface of the longitudinal members is substantially flush with the upper surface of the transverse members for support of the floor thereacross; access means within the housing for ingress and egress of a person into and out of the interior of the housing; a seat within the housing for supporting a person having a position adjustable backrest; a locking assembly for releasably locking the backrest in a plurality of positions, the locking assembly including a tracking guide attached to the backrest comprising a U-shaped member having a rod for securing the backrest in one of the plurality of positions, and a locking bracket releasably engaging the tracking guide for securing the backrest in said plurality of positions, the locking bracket including an outer member, an inner member received within the outer member forming a channel therebetween receiving the rod of the tracking guide, a pivotable member overlying the channel, the pivotable member having a plurality of openings for receiving the rod for securing the backrest in one of the plurality of positions and a flange overlying a portion of the inner member, and securing means for releasably securing the flange to the portion of the inner member; treatment means within the housing for treating the contaminated environment within the interior of the housing resulting from the presence of a person therein having a communicable disease, the treatment means comprising a primary filter for treatment of contaminated air within the housing, a first frame overlying one surface of the primary filter having an opening in communication therewith for the flow of contaminated air therethrough, a prefilter overlying the opening within the first frame, and a second frame overlying one surface of the prefilter having an opening in communication therewith for the flow of contaminated air therethrough, the second frame having one portion releasably secured by a U-shaped member extending outwardly along one side of the first frame and another portion engaging a portion of the housing for releasably securing the second frame threat, whereby the primary filter and the prefilter are accessible for replacement upon removal of the first and second frames; and means within the housing for drawing contaminated air from within the housing through both the prefilter and the primary filter and discharging clean filtered air to the surrounding environment outside the housing.

BRIEF DESCRIPTION OF THE DRAWINGS

The above description, as well as further objects, features and advantages of the present invention will be more fully understood with reference to the following detailed description of a treatment booth for infectious patients, when taken in conjunction with the accompanying drawings, wherein.

DETAILED DESCRIPTION OF THE PREFERRED EMBODIMENTS

Figure 1:
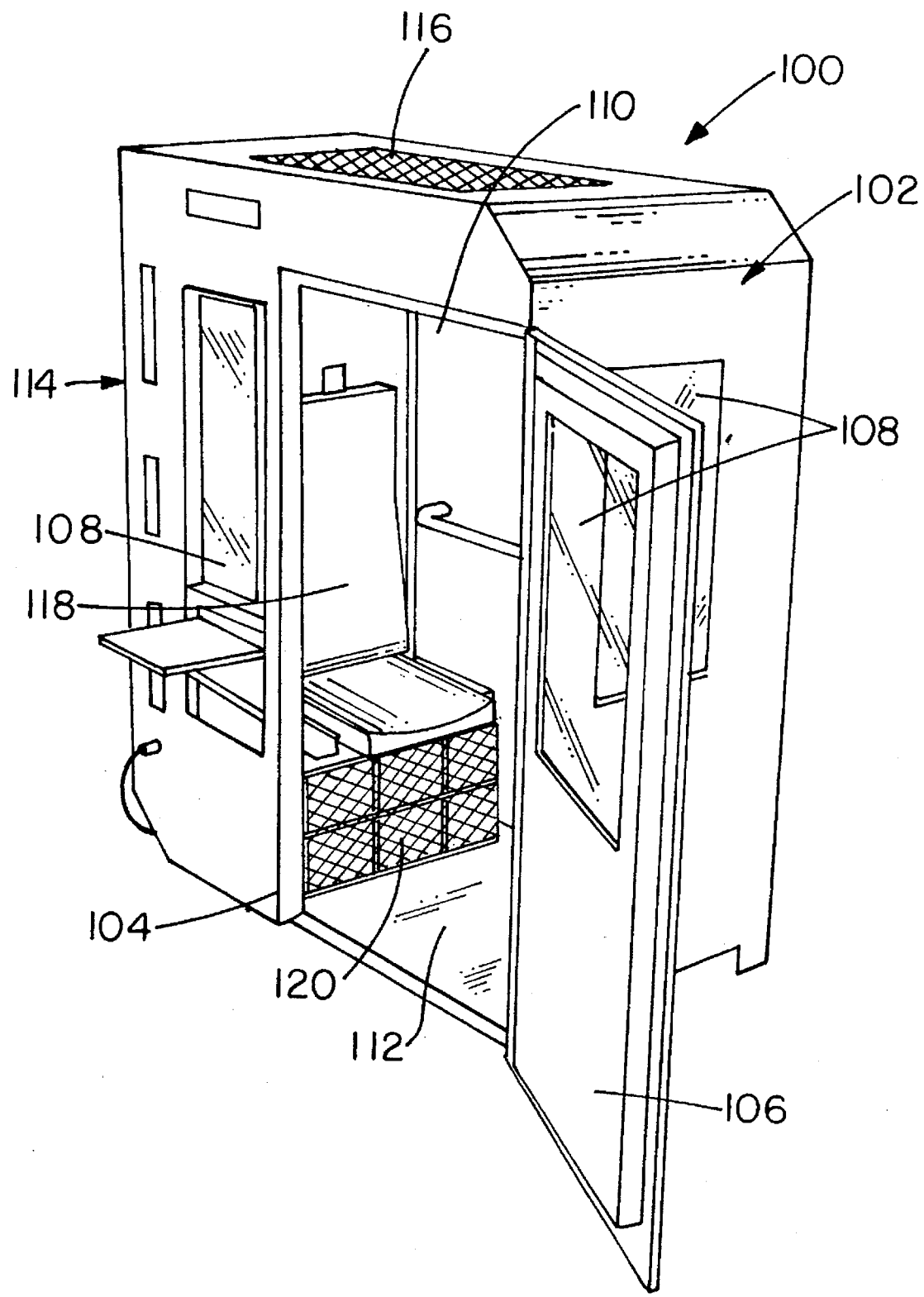
FIG. 1 is a perspective view of a sputum induction/aerosol treatment booth constructed in accordance with one embodiment of the present invention.

Referring now to the drawings, wherein like reference numerals represent like elements, there is shown in FIG. 1 a sputum induction/aerosol treatment booth generally designated by reference numeral 100 for sputum induction and aerosolized treatment of a patient having a communicable disease. The booth 100 is generally constructed from a housing 102 formed from an outer shell 104 of durable heavy galvannel steel with a two-part molecularly bonded, scratch-resistant finish that is easy to maintain and clean. A door 106 and plural windows 108 are tightly fitted within the outer shell 104 to prevent air leakage. The interior walls 110 and floor 112 of the booth 100 are constructed from high quality non-porous stainless steel to create an easily cleanable environment. An outside work station generally designated by reference numeral 114 provides a full view of all monitoring systems and has two ports for procedures. The station 114 also includes other features, for example, a task light, pull-out shelf, hospital grade power cord and two ground fault interrupt power outlets. The top of the housing 102 supports an inlet filter assembly 116, while the interior of the housing supports a seat assembly 118 and a HEPA filter assembly 120.

Figure 2:
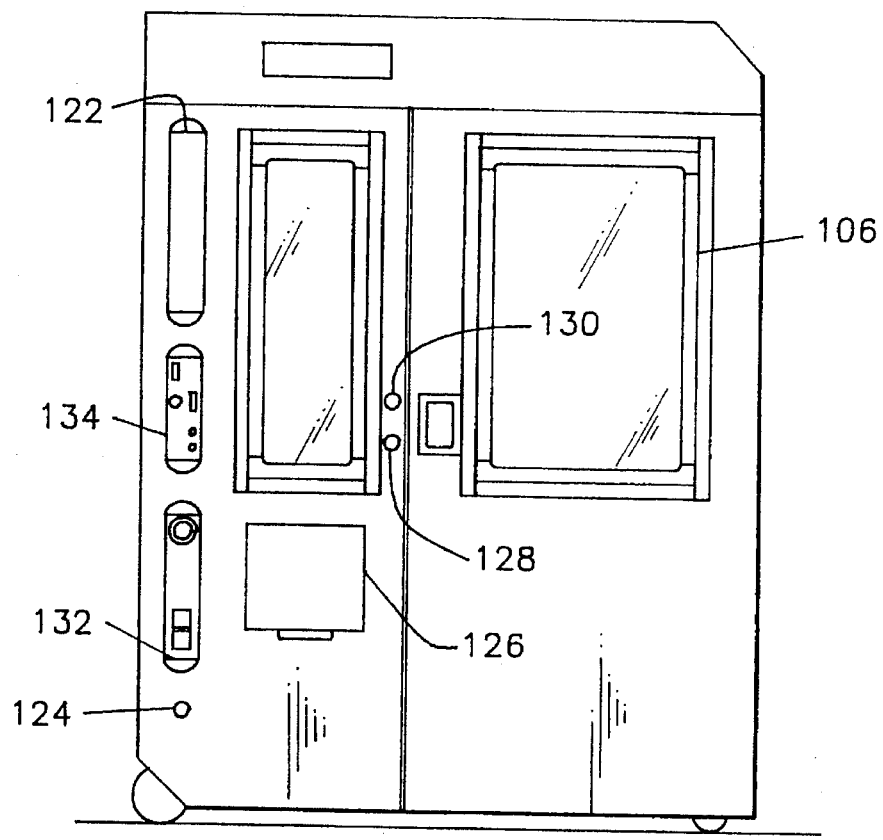
FIG. 2 is a front elevational view of the exterior of the sputum induction/aerosol treatment booth.

Referring to FIG. 2, the outside work station 114 is shown in greater detail. For example, the outside work station 114 includes a ballast access panel 122, a detachable power cord 124, a flush pull-out shelf 126, a sputum treatment port 128, an aerosolized drug treatment port 130, and a pair of control panels 132, 134. Control panel 134 includes, for example, a booth power switch, a ground fault interrupt duplex receptacle, and an operational hour meter indicating the operating time of each individual booth. Control panel 134 includes, for example, a UV lighting on/off switch, an audible alarm system operative with respect to the blower airflow reaching proper levels within the booth, and door indicator lamps with respect to its open/closed position. It is to be understood that other control features designed for use with the sputum induction/aerosol treatment booth 100 of the present invention may be included within the outside work station 114 as desired. For sputum induction, the patient within the booth 100 is provided with a container for expectoration. A flexible hose is attached to a hard plastic sputum adapter which is placed in the sputum treatment port 128. An outside hose is attached to a nebulizer while the inside flexible hose extending from the sputum adapter is attached to a sputum induction mask. With door 106 closed, sputum induction procedures are administered to the patient. The sputum container is left inside the booth 100 by the patient. Disposal of patient materials should preferably be in accordance with the facility's infection control procedures. In particular, the sputum adapter should be treated as disposable medical waste.

For aerosolized treatment, an air line is threaded through an adapter sleeve, which is then slid through the sputum adapter. The sputum adapter with air line extending therethrough is received within the aerosolizing drug treatment port 130, or optionally the sputum treatment port 128. The patient is seated within the booth 100 with the seat assembly 118 being adjusted to the appropriate position for the procedure being provided. In particular, the seat assembly 118 should be an upright position for sputum induction, while the seat assembly may be reclined for aerosolized drug treatment. An individualized mask system is attached to the patient for inhalation. With the door 106 closed, aerosolized drug is administered by means of a nebulizer through the air line to the patient. When the procedure is completed, the air line is disconnected from the nebulizer and the patient should pull the line into the booth 100 for disposal with other materials in accordance with the facility's infectious control procedures. Once again, it is recommended that the sputum adapter and adapter sleeve be treated as disposable medical waste.

Figure 3:
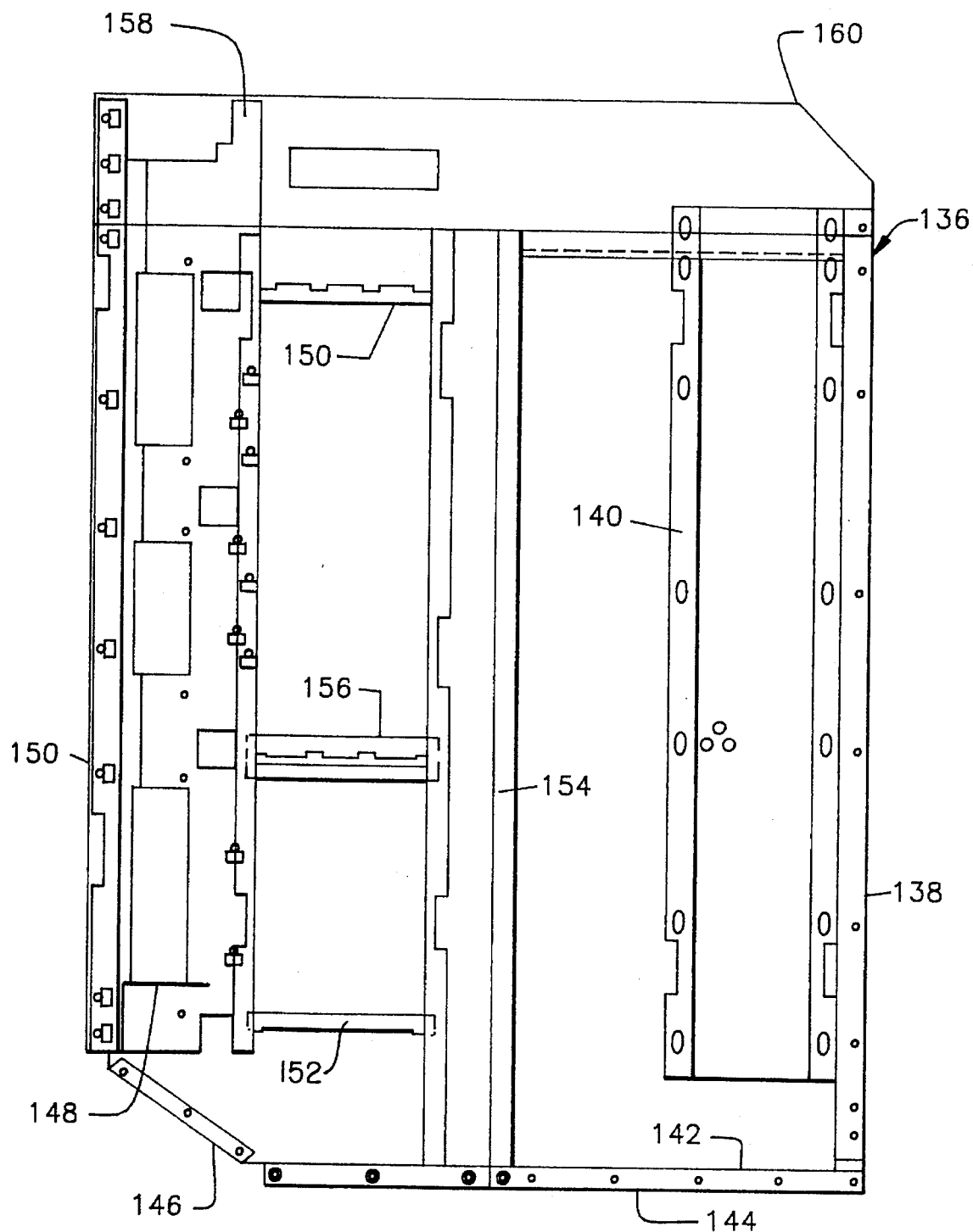
FIG. 3 is a front elevational view of the skeletal support framing for the sputum induction/aerosol treatment booth.

Referring now to FIG. 3, the housing 102 is provided with a support skeletal framing in the nature of a skeletal structure 136. For example, the skeletal structure 136 includes a forward viewing wall 138, a grab bar stiffener 140, a floor panel 142 overlying a floor regress angle 144, a rear caster mounting plate 146, a duct work mounting plate 148, a blower wall panel 150, a table cut-out back 152, a longitudinal door jamb 154, upper/lower window frames 156, stiffener 158 for front wall at seat location, transom panel 160, etc. As shown, the transom panel 160 extends entirely from one end of the housing 102 from forward viewing wall 138 to a location beyond the longitudinal door jamb 154, and preferably, to the blower wall panel 150. By extending the transom panel 160 beyond the extent of the longitudinal door jamb 154, the transom panel provides enhanced rigidity to the skeletal structure 136.

Figure 4:
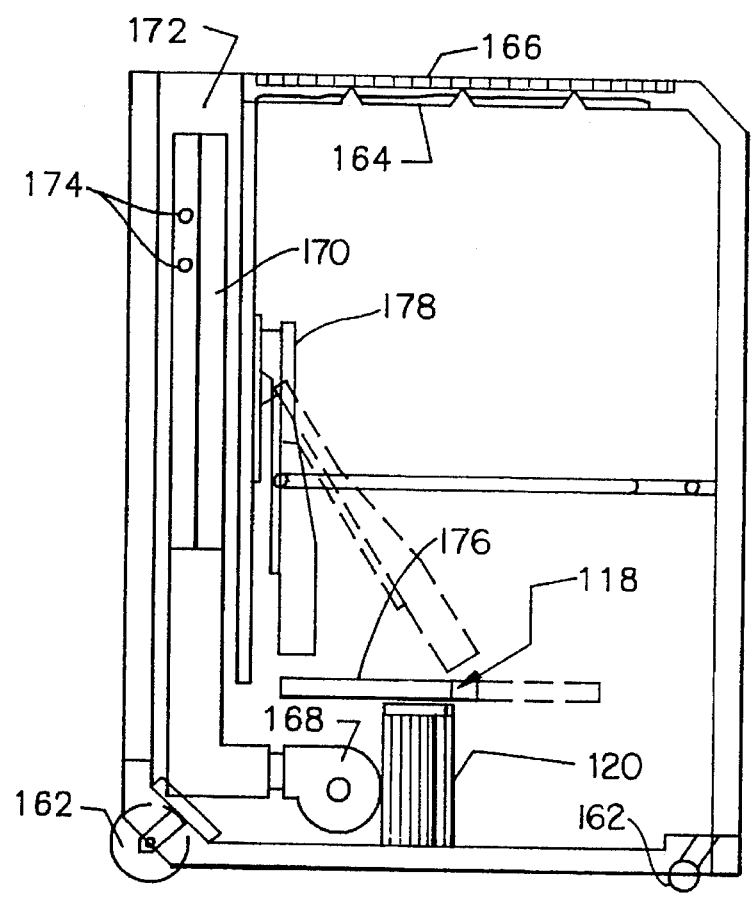
FIG. 4 is a front elevational view of the interior of the sputum induction/aerosol treatment booth.

Referring to FIG. 4, the booth 100 is provided with forward and rear casters 162 to enable relocation of the booth to an appropriate location for patient treatment. The inlet filter assembly 116 is constructed from a perforated plate 164 for supporting an air filter 166 for filtering air being drawn into the interior of the booth 100 by means of blower assembly 168. Contaminated air within the booth 100 is drawn into the blower assembly 168 through the filter assembly 120 which removes hazardous microbial airborne particles which may include infectious respiratory organisms. Filtered air is discharged by the blower assembly 168 upwardly through exhaust duct 170 to the surrounding environment via opening 172. Positioned within the duct 170 are one or more cold cathode germicidal ultraviolet lamps 174. The ultraviolet lamps 174 are effective for their germicidal ultraviolet radiation in killing airborne bacteria. The ultraviolet lamps 174 provide a degree of redundancy as hazardous microbial airborne particles will typically not pass through the filter assembly 120. The seat assembly 118 is constructed from a seat 176 moveably arranged overlying the filter assembly 120 and a backrest 178 positioned forward of the duct 170 of the blower assembly 168. As illustrated by the phantom lines, the seat assembly 118 is adjustable for positioning the backrest 178 in a plurality of inclined positions.

Figure 5:
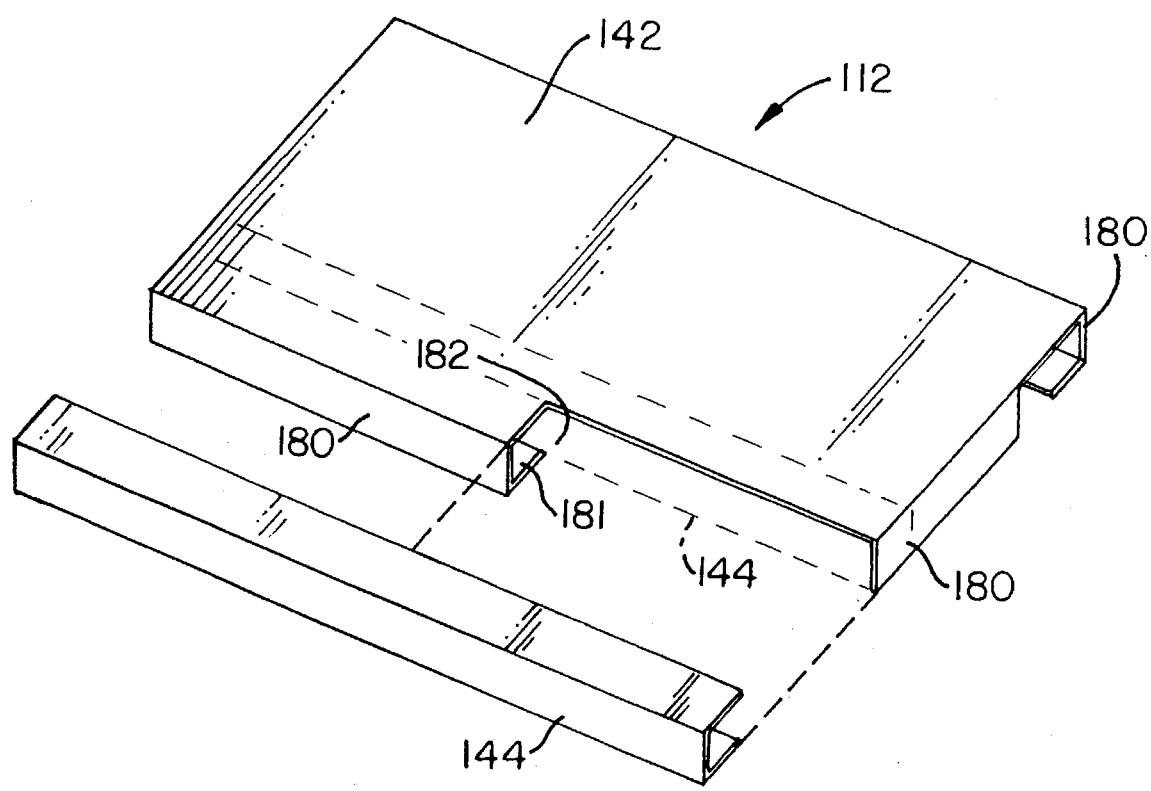
FIG. 5 is a perspective view of a floor panel for the sputum induction/aerosol treatment booth.
Figure 6:
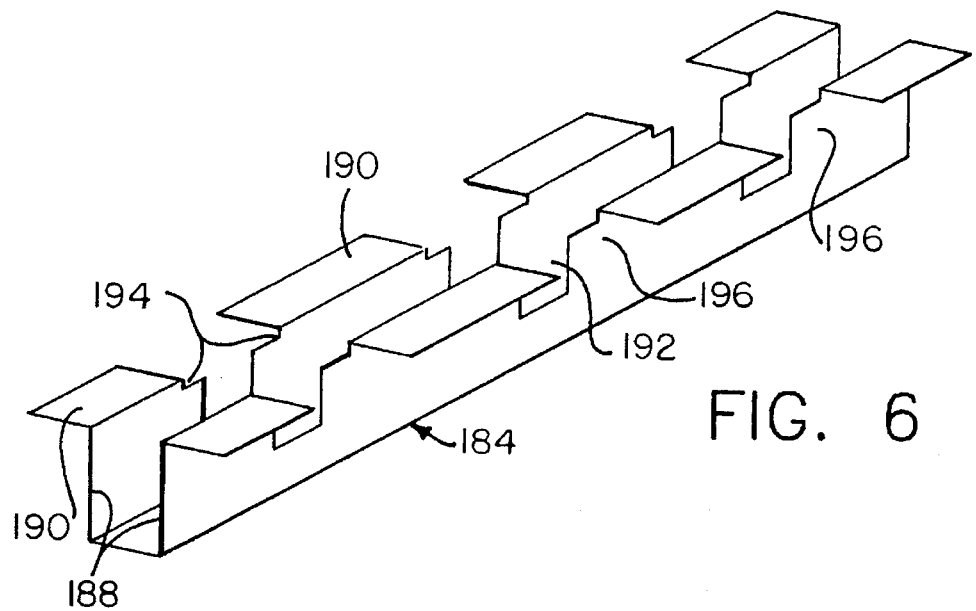
FIG. 6 is a perspective view of an elongated floor panel support member.
Figure 7:
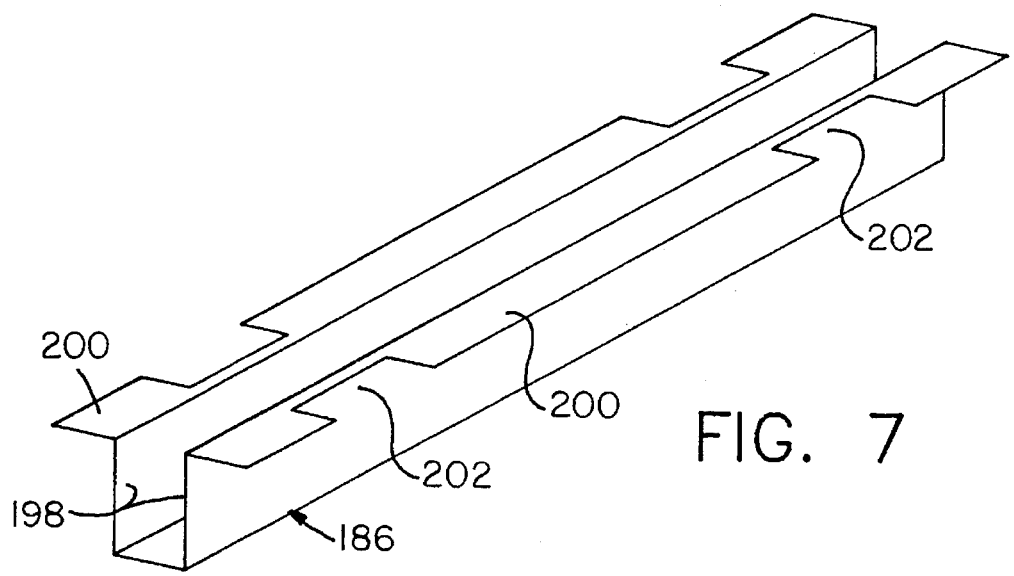
FIG. 7 is a perspective view of another elongated floor panel support member.
Figure 8:
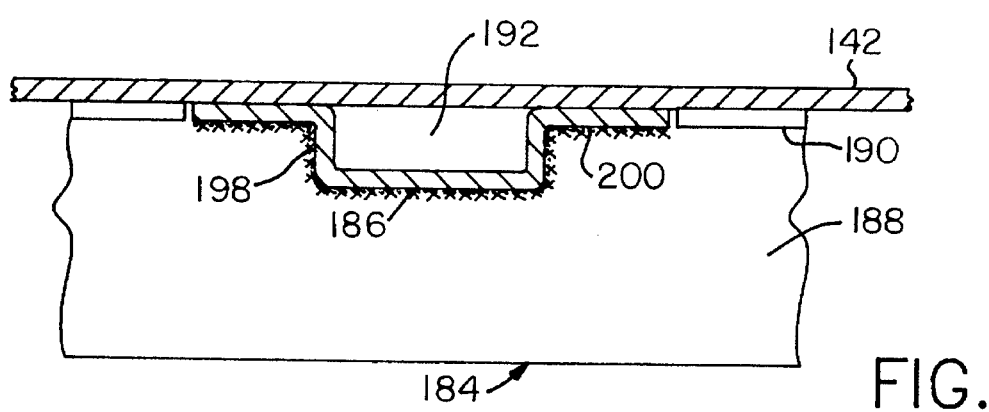
FIG. 8 is a cross-sectional view showing the assembled relationship between the floor panel support members.
Figure 9:
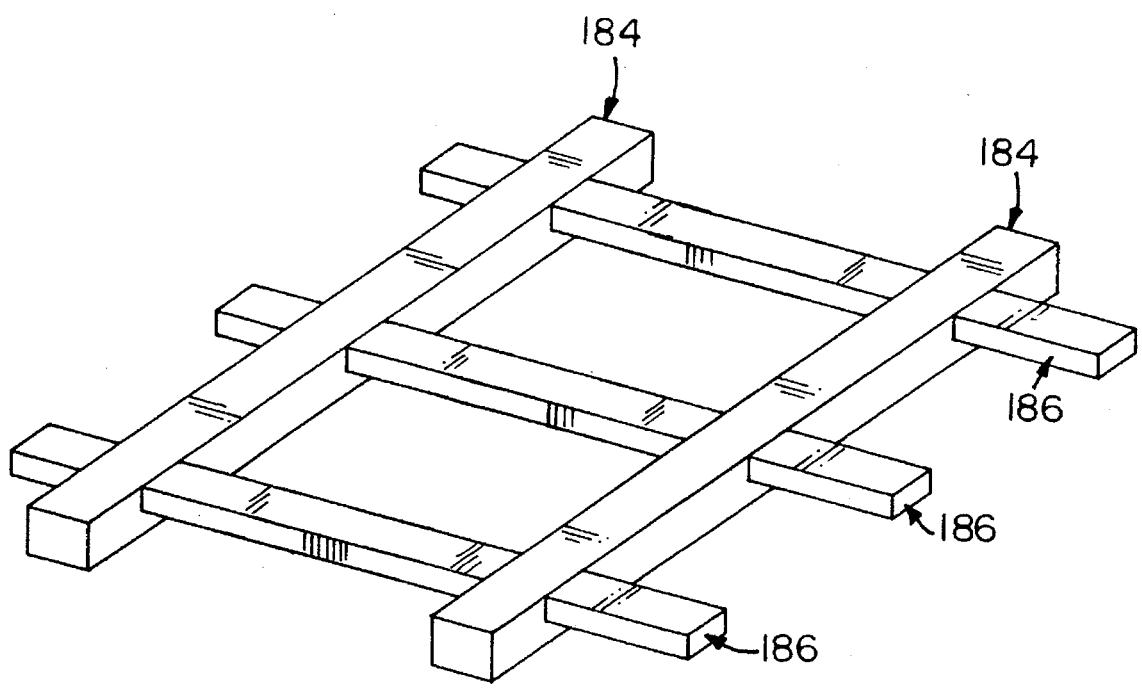
FIG. 9 is a perspective view of the assembled relationship of the floor panel support members arranged in a grid.

Referring to FIGS. 5–9, there will be described the construction of the floor 112 adapted to support a patient and one or more attending physicians. As shown in FIG. 5, the floor 112 is constructed from a floor panel 142 having downwardly bent peripheral walls 180 with inwardly turned flanges 181 to provide the floor panel with increased rigidity and mechanical strength. Adjacent the location of the door 106, the floor panel 142 is provided with an elongated notch 182. The floor panel 142 is supported along the notch 182 by the floor regress angle 144 which is constructed in the nature of a U-shaped channel similar to the lateral peripheral walls 180. The floor panel 142 is rigidly supported by a plurality of elongated longitudinal floor panel support members 184 (see FIG. 6) and elongated transverse floor panel support members 186 (see FIG. 7) assembled as shown in FIG. 8 in a grid arrangement (see FIG. 9).

The longitudinal support members 184 as shown in FIG. 6 are constructed as a generally U-shaped member having depending spaced sidewalls 188 from which there outwardly extends in transverse relationship flanges 190. A plurality of rectangular openings 192 are provided spaced along the sidewalls 188 bound on either side by a shallow notch 194. An opening 196 is provided within the flanges 190 coextensive with the openings 192 and notches 194. It is to be understood that the notches 194 may have been either formed as cut-outs in the sidewalls 188 or resulting from the thickness of the flanges when bent extending outwardly from the sidewalls 188. The transverse support members 186 as shown in FIG. 7 are also formed as generally U-shaped members having spaced apart sidewalls 198 from which there outwardly extends flanges 200 in transverse arrangement. Spaced along the flanges 200 are a plurality of generally rectangular shaped openings 202. As shown in the drawings, the transverse support members 186 are shallower than the longitudinal support members 184. In particular, the depth of the transverse support members 186 generally corresponds to the height of rectangular openings 192 within the longitudinal support members 184.

The longitudinal support members 184 are arranged in parallel spaced apart relationship in a plurality of either rows or columns. The transverse support members 186 are positioned perpendicular to the longitudinal support members 184 so as to be received within the rectangular openings 192 as shown in FIG. 8. In this regard, the flanges 200 of the transverse support members 186 are received within the notches 194 on either side of the rectangular openings 192. As a result of this nesting arrangement of the transverse support members 186 within the rectangular openings 192 and notches 194 of the longitudinal support members 184, the upper surface of the longitudinal and transverse support members are substantially flush with each other so as to uniformly support the floor panel 142 thereon. The longitudinal support members 184 may be secured to the transverse support members 186 by welding around the engaged portions therebetween, such as those locations designated by an "X" in FIG. 8.

The grid of assembled longitudinal and transverse support members 184, 186 provides a rigid support for the floor panel 142 for supporting one or more occupants of the booth 100. The grid may be supported by the floor 112 as shown in FIG. 5 by having the ends of, for example, the transverse support members 186 being captured and supported upon the inwardly extending flanges 181 of the peripheral walls 180, as well as within the spaced apart sidewalls of the floor regress angle 144. The resulting construction of the floor 112 will resist bowing even when carrying extreme loads so as to maintain the structural integrity of the booth 100 during use.

Figure 10:
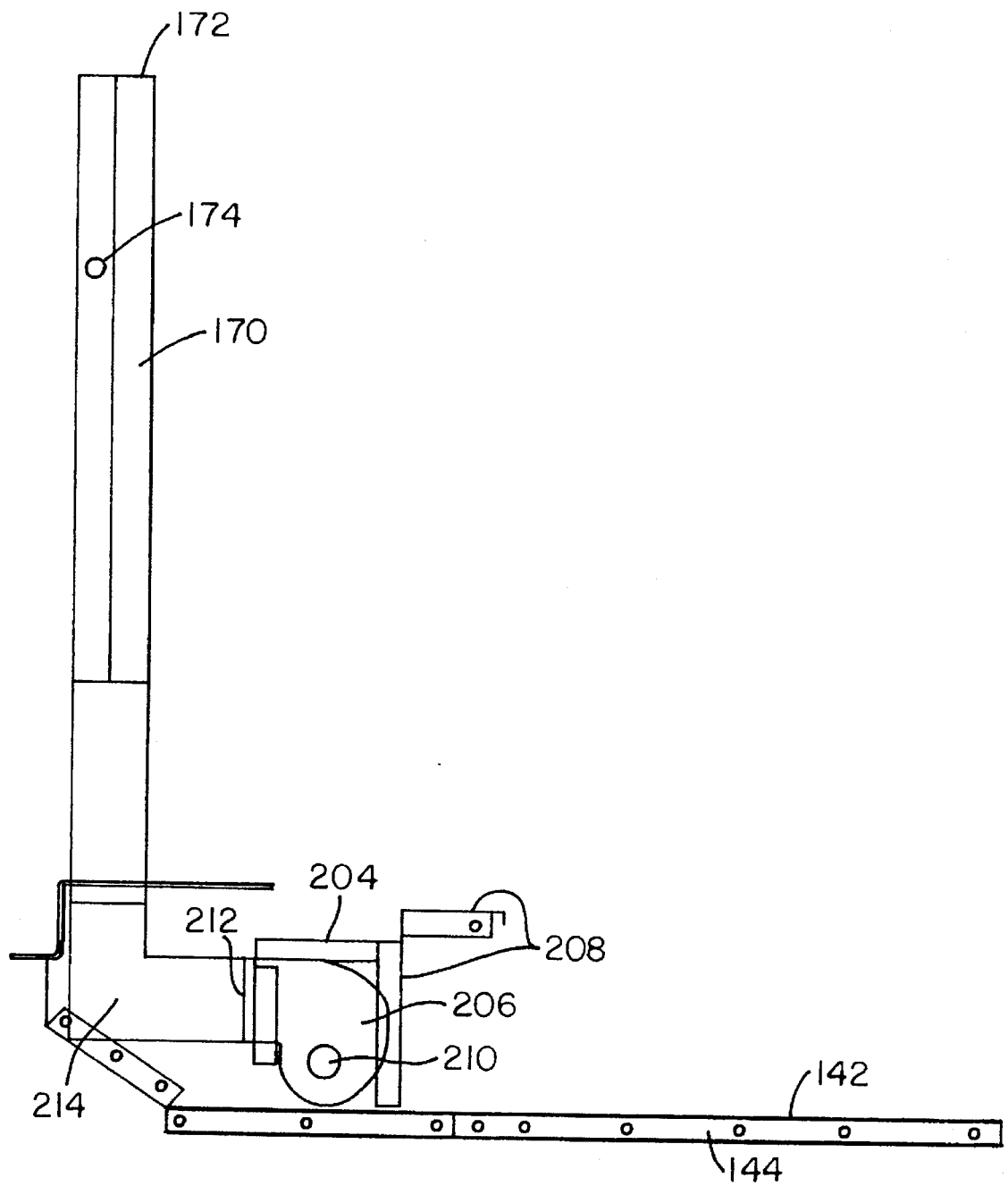
FIG. 10 is a front elevational view of the ventilation system of the sputum induction/aerosol treatment booth.
Figure 13:
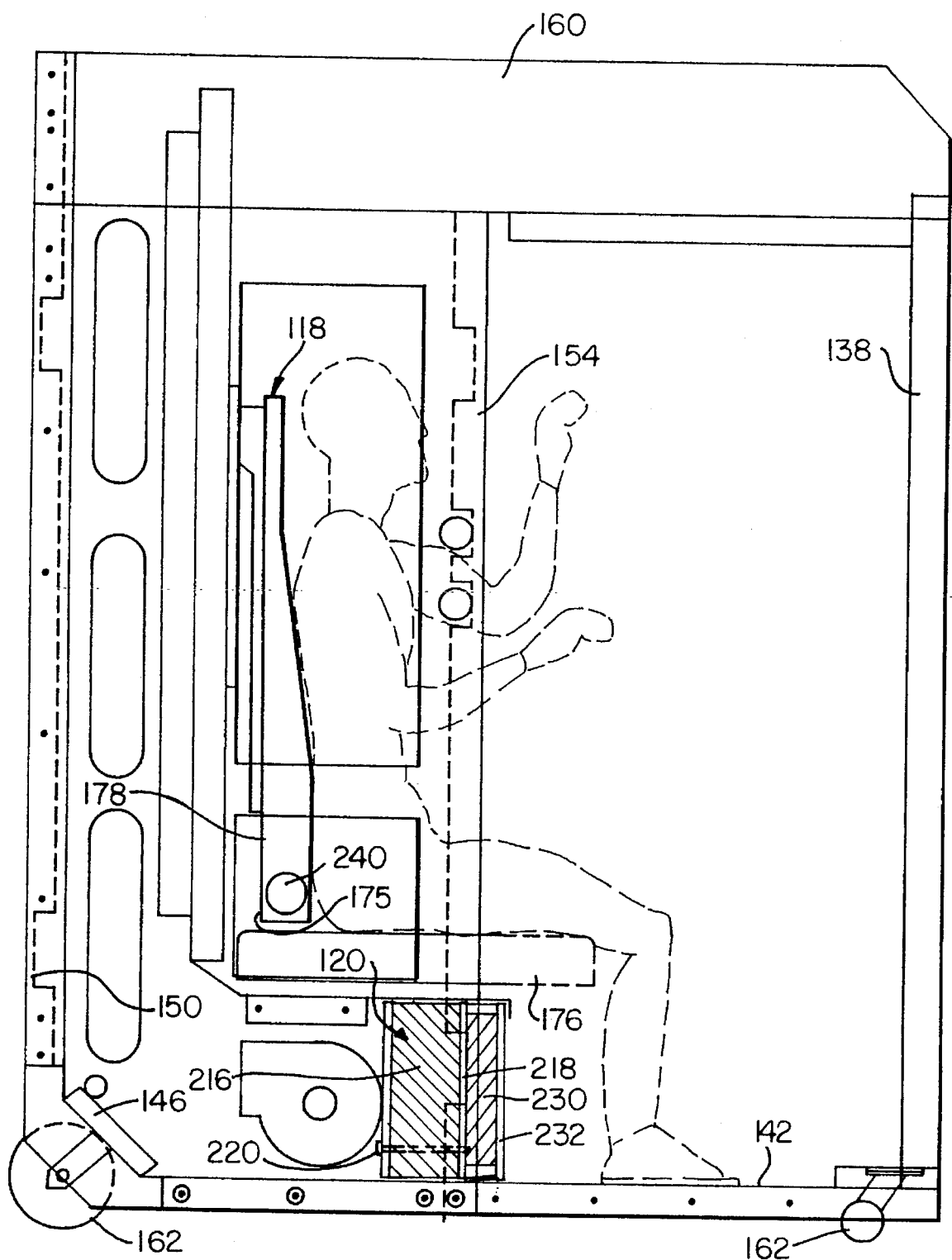
FIG. 13 is a front elevational view showing a seat having a backrest releasably secured in a vertical position.

Referring to FIG. 10, there now will be described the construction of the blower assembly 168. The blower assembly 168 includes a blower housing cradle 204 which contains a blower 206. The blower 206 is positioned rearwardly of an air filter stop 208. The blower 206 has an inlet 210 for drawing air within the interior of the booth 100 through the filter assembly 120 positioned adjacent the air filter stop 208 as shown in FIG. 13. The outlet 212 of the blower 206 is connected to an exhaust duct elbow 214 which, in turn, is connected to the vertically arranged exhaust duct 170. Adjacent the outlet opening 172 of the exhaust duct 170 there is internally provided one or more UV lamps 174 of the type previously described. In this manner contaminated air containing hazardous microbial airborne particles which may include infectious respiratory organisms can be withdrawn through the filter assembly 120 for removal, subsequently exposed to the ultraviolet lamps 174 for additional efficacy and discharge to the surrounding environment.

Figure 11:
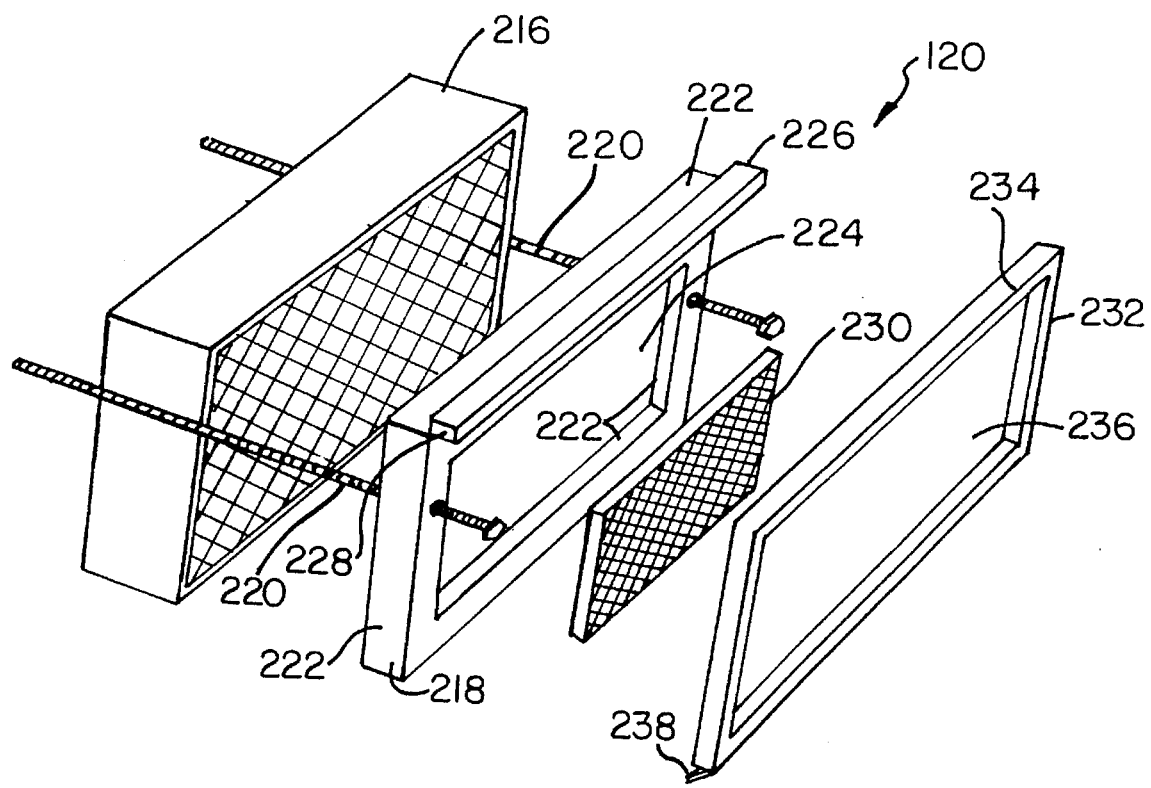
FIG. 11 is a perspective, exploded unassembled view of a HEPA filter assembly for removable installation within the sputum induction/aerosol treatment booth.
Figure 12:
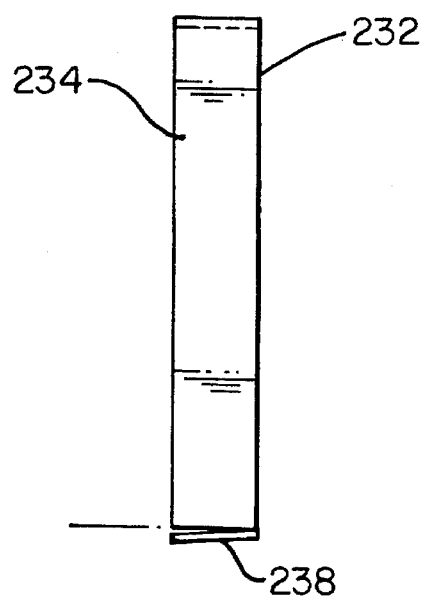
FIG. 12 is a side elevational view of a frame forming a portion of the HEPA filter assembly.

The filter assembly 120 is more clearly shown in FIGS. 11–13. The filter assembly 120 initially includes a HEPA filter 216. HEPA filters have been widely utilized in the medical, health care and pharmaceutical fields as a means to entrap airborne particles in the submicron range. This type of filter is widely recognized and has been specified in federal, military and pharmaceutical standards for more than thirty years. The HEPA filter 216 is constructed of extremely large concentrations of randomly oriented boron silicate fibers. This filtration media consists typically of 100% glass microfibers which range in mean diameter from 0.26–7 microns in size. Acrylic resin binders bond the various controlled blends of several glass fiber diameters to create a mat and matrix composed of numerous passages. The smaller the fiber diameter, the greater the capture and containment of smaller particles and the higher the efficiency of the filter. Preferably, the HEPA filter 216 is capable of a minimum efficiency of 99.97% on 0.3 micron size particles, which provides a degree of filtration environments where airborne bacterial concentrations pose a hazard to patients, health care workers and the like. In addition, the HEPA filter 216 is capable of removing other airborne contaminants such as dust, pollen, mold, spores and the like.

The HEPA filter 216 is removably held in place underlying the air filter stop 208 adjacent the blower housing cradle 204 by means of a first rectangular frame 218 and a pair of bolts 220. The frame 218 is circumferentially surrounded by rearwardly extending sidewalls 222 and includes a central rectangular opening 224. The bolts 220 extend through the frame 218 adjacent the opening 224 and next to the HEPA filter 216 for securing to a portion of the air filter stop 208. Along the upper portion of the frame 218 there is provided a downwardly facing U-shaped member 226 extending outwardly forming an elongated opening 228.

A prefilter 230 is positioned overlying the opening 224 within the frame 218. Typically, for example, the prefilter 230 is of a low efficiency type having a particle retention size in the range of 10–15 microns or larger for trapping conventional airborne particles such as lint, dust, pollen and the like. The prefilter 230 is held in position by a second rectangular frame 232. The second frame is provided with surrounding rearwardly extending sidewalls 234 and a central rectangular opening 236. The bottom sidewall designated separately by reference numeral 238 is bent outwardly at an angle unlike the remaining sidewalls 234. The frame 232 is held in position by the combination of the U-shaped member 226 and the floor panel 142.

Specifically, the upper edge of the frame 232 is initially captured within the elongated opening 228 provided by the U-shaped member 226. This is achieved by tilting the frame 232 into position underlying the U-shaped member 226. As the bottom of the frame 232 is swung towards a position overlying the first frame 218, the angled sidewall 238 engages the floor panel 142. Continued movement of the frame 232 causes compression of the angled sidewall 238 upwardly until the frame 232 is positioned snugly adjacent the first frame 218 thereby capturing and holding the prefilter 230 in place. The angled sidewall 238 functions as a compression spring to force the second frame 232 upward into the U-shaped member 226 for retention thereat. Based upon this construction, the prefilter 230 and HEPA filter 216 may be easily replaced when and as required.

Figure 14:
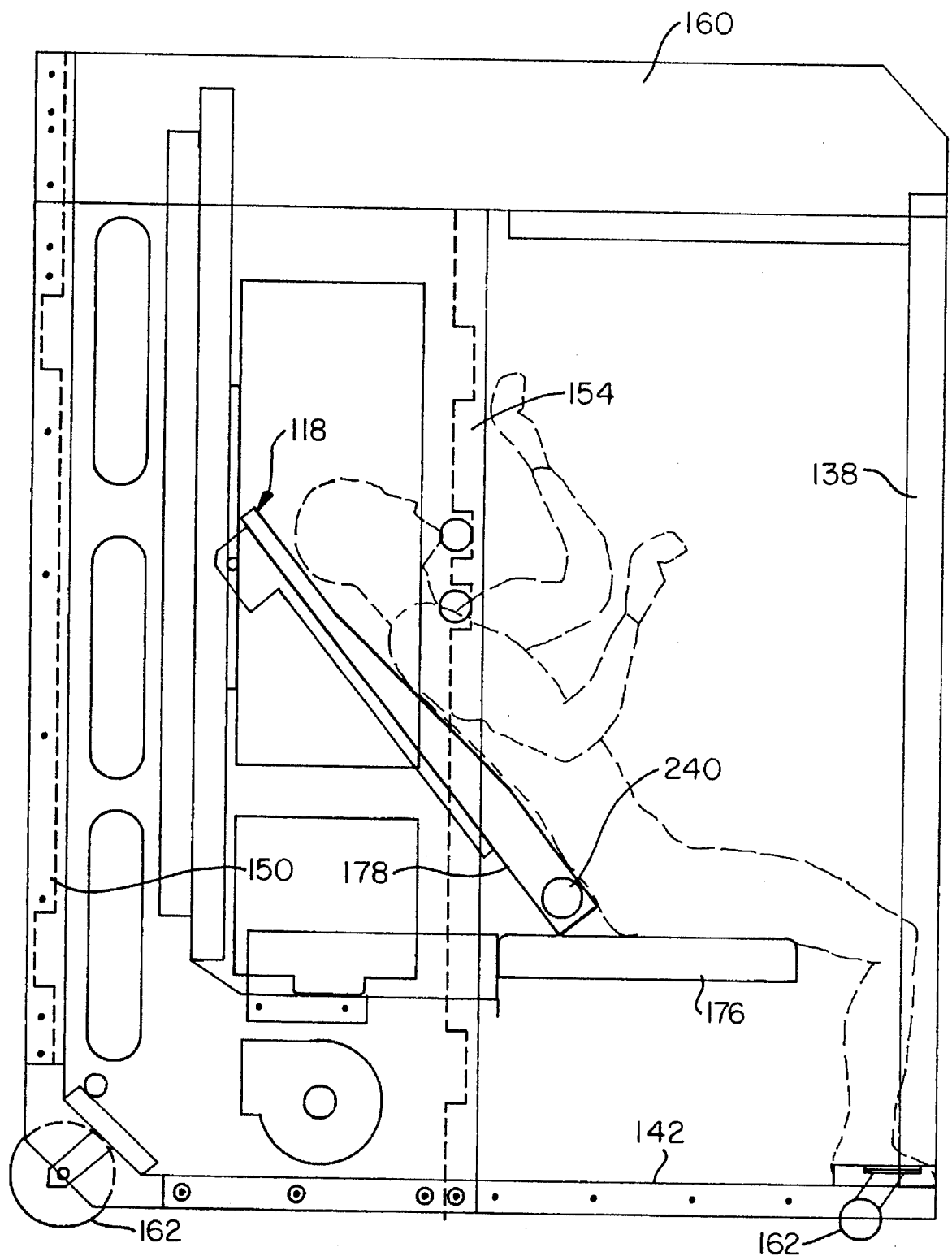
FIG. 14 is a front elevational view showing the seat having the backrest releasably secured in one of a plurality of inclined positions.

Turning to FIGS. 13 and 14, the seat assembly 118 is illustrated in a plurality of alternative positions or orientations. For example, in FIG. 13 the seat assembly is arranged with the backrest 178 in a vertical position. This position is generally preferred for sputum induction procedures. On the other hand, as shown in FIG. 14 the backrest 178 is arranged at an inclined angle to enable the patient to recline. This position is generally preferred for aerosolized drug treatment. The seat 176 is slidable in a horizontal orientation by being supported, for example, rollers, ball bearings, etc. (not shown) or otherwise using known slidable mechanisms. The backrest 178, on the other hand, has its lower end pivoted at location 240 to a portion of the seat assembly 118. The upper end of the backrest 178 is constructed to be releasably fixed at a plurality of vertical locations so as to enable adjusting the angular position or incline of the backrest.

Figure 15:
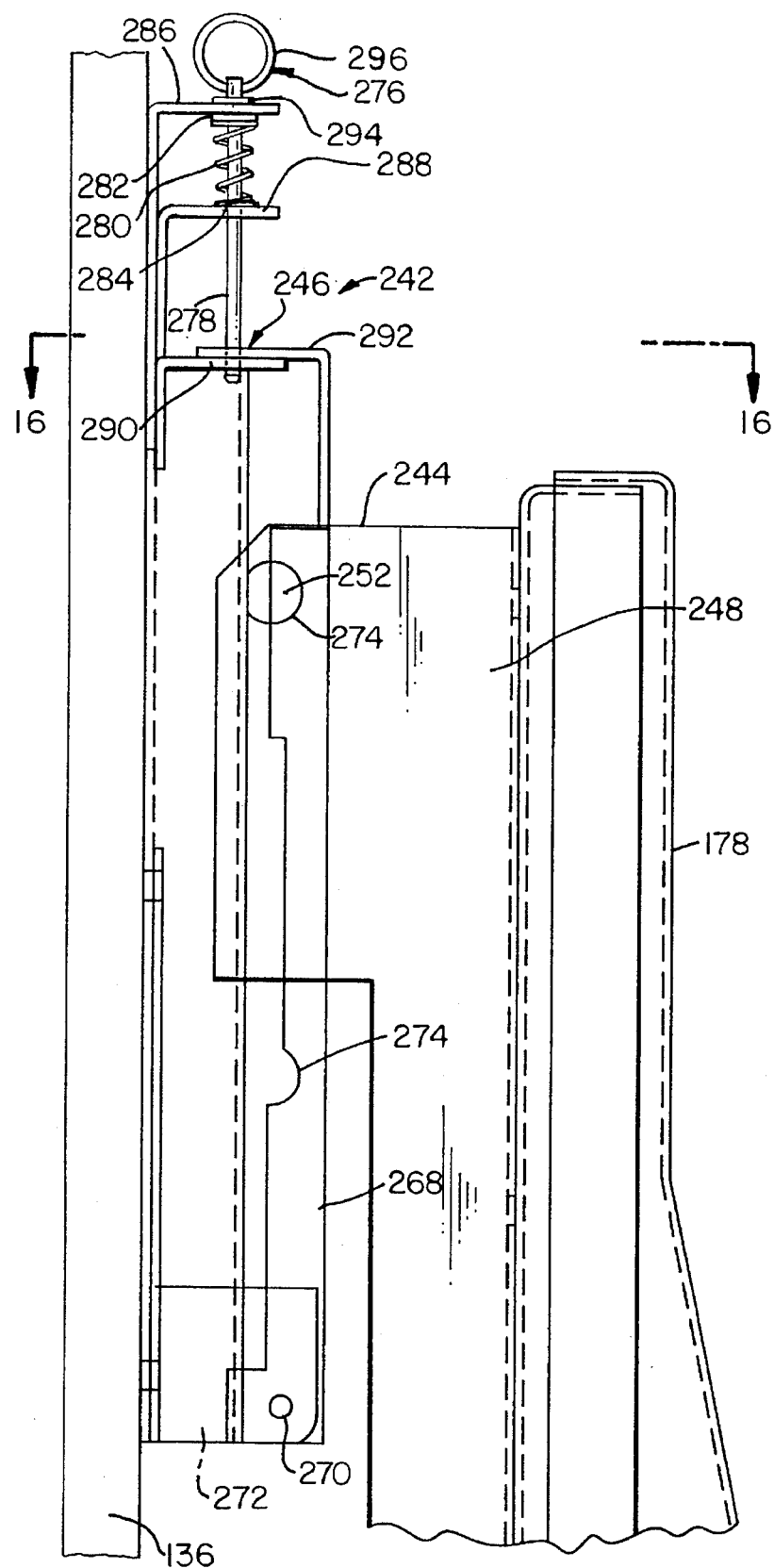
FIG. 15 is a front elevational view of a locking assembly for securing the backrest in the plurality of positions.
Figure 16:
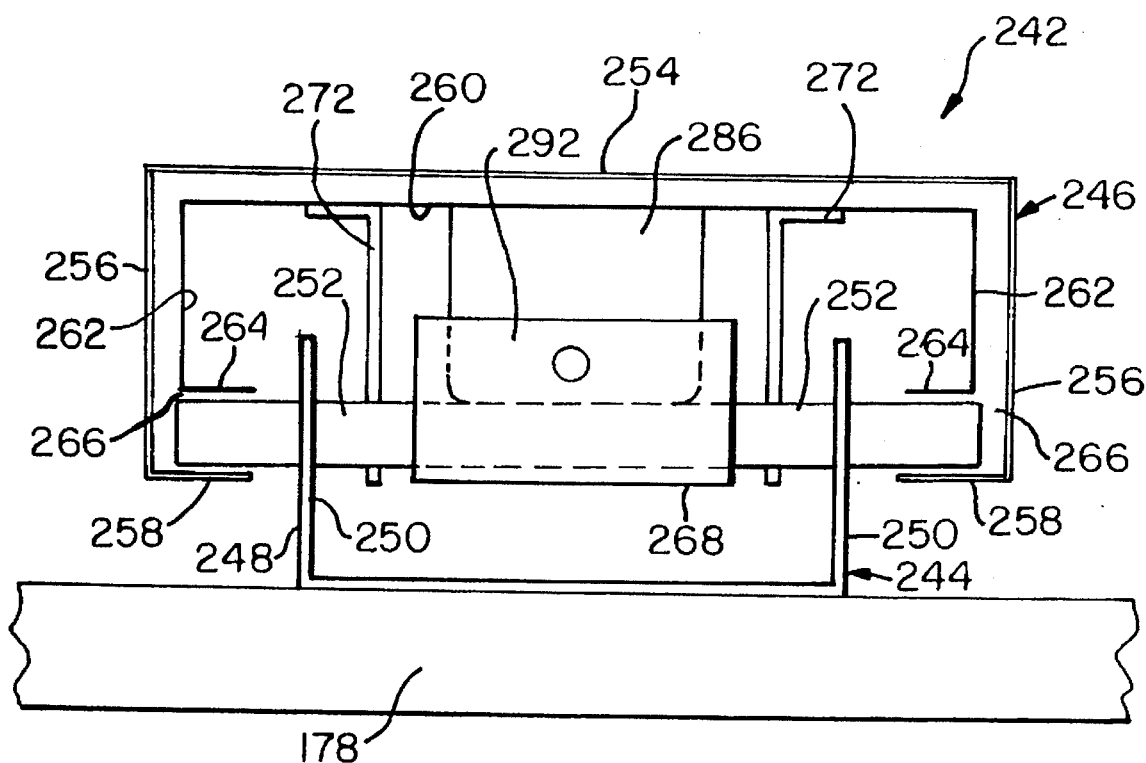
FIG. 16 is a partial cross-sectional view taken along line 16—16 in FIG. 15 of the locking assembly constructed from a tracking guide attached to the backrest and a locking bracket releasably engaging the tracking guide for securing the backrest in the plurality of positions.

As more clearly shown in FIGS. 15 and 16, there is shown the construction of a locking assembly 242 for releasably locking the backrest 178 in a plurality of positions. The locking assembly 242 is constructed from a tracking guide 244 attached to the backrest 178 and a locking bracket 246 attached to the skeletal structure 136 adapted for releasably engaging the tracking guide 244 for securing the backrest 178 in a plurality of positions. The tracking guide 244 includes a U-shaped member 248 attached to the back of the backrest 178. The U-shaped member 248 includes a pair of spaced apart sidewalls 250 through which there extends at an upper end thereof a longitudinally extending rod 252. As shown in FIG. 16, the rod 252 extends outwardly beyond the extent of the sidewalls 250.

The locking bracket 246 is constructed from an outer generally U-shaped member 254 having a pair of spaced apart sidewalls 256 and inwardly turned flanges 258. Nested within the U-shaped member 254 is a second U-shaped member 260 also including a pair of spaced apart sidewalls 262 and inwardly turned flanges 264. The inwardly turned flanges 258, 264 provide a vertical channel 266 therebetween adapted to slidingly receive the rod 252 of the tracking guide 244. It will be appreciated that as the backrest 178 is positioned between various angular positions, the rod 252 slides up and down captured within the channel 266 as a guide.

A U-shaped locking bar 268 is pivotably arranged overlying rod 252 of the tracking guide 244 interiorly between the sidewalls 250. The locking bar 268 is pivotable at its lower end about a shaft 270 supported by a pair of spaced apart L-shaped brackets 272 mounted to the skeletal frame 136 within the interior of the nested U-shaped members 254, 260. The forward edges of the locking bar 268 are provided with a plurality of spaced apart notches 274 sized to partially capture the rod 252.

The locking bar 268 is releasably held in locked position by means of securing pin assembly 276. The pin assembly 276 is constructed from a shaft 278 which receives a compression spring 280 held in place between a pair of spaced washers 282, 284. The shaft 278 is received longitudinally through a plurality of aligned openings within the locking bracket 246. More specifically, U-shaped member 254 includes an upward extension provided with a horizontal flange 286 having an opening therein. An L-shaped bracket 288 is secured to the U-shaped member 254 spaced underlying flange 286 and provided with an aligned opening. A second L-shaped bracket 290 is similarly secured spaced underlying bracket 288 and having an aligned opening. Locking bar 268 is provided at its upward end with an inwardly extending horizontal flange 292 having an opening alignable with the opening within the bracket 290 when arranged overlying therewith as shown in FIG. 15.

Shaft 278 is held in position within the aligned openings by the spring 280 outwardly compressing washer 282 against flange 286 and washer 284 against bracket 288. The shaft 278 extends downwardly through the aligned openings within the bracket 290 and flange 292 of the locking bar 268 to maintain the locking bracket in closed position for securing the backrest 174 in one of a plurality of positions. A washer 294 secured about the top of the shaft 278 limits the vertical travel of the shaft in a downward direction upon engaging flange 286.

Figure 17:
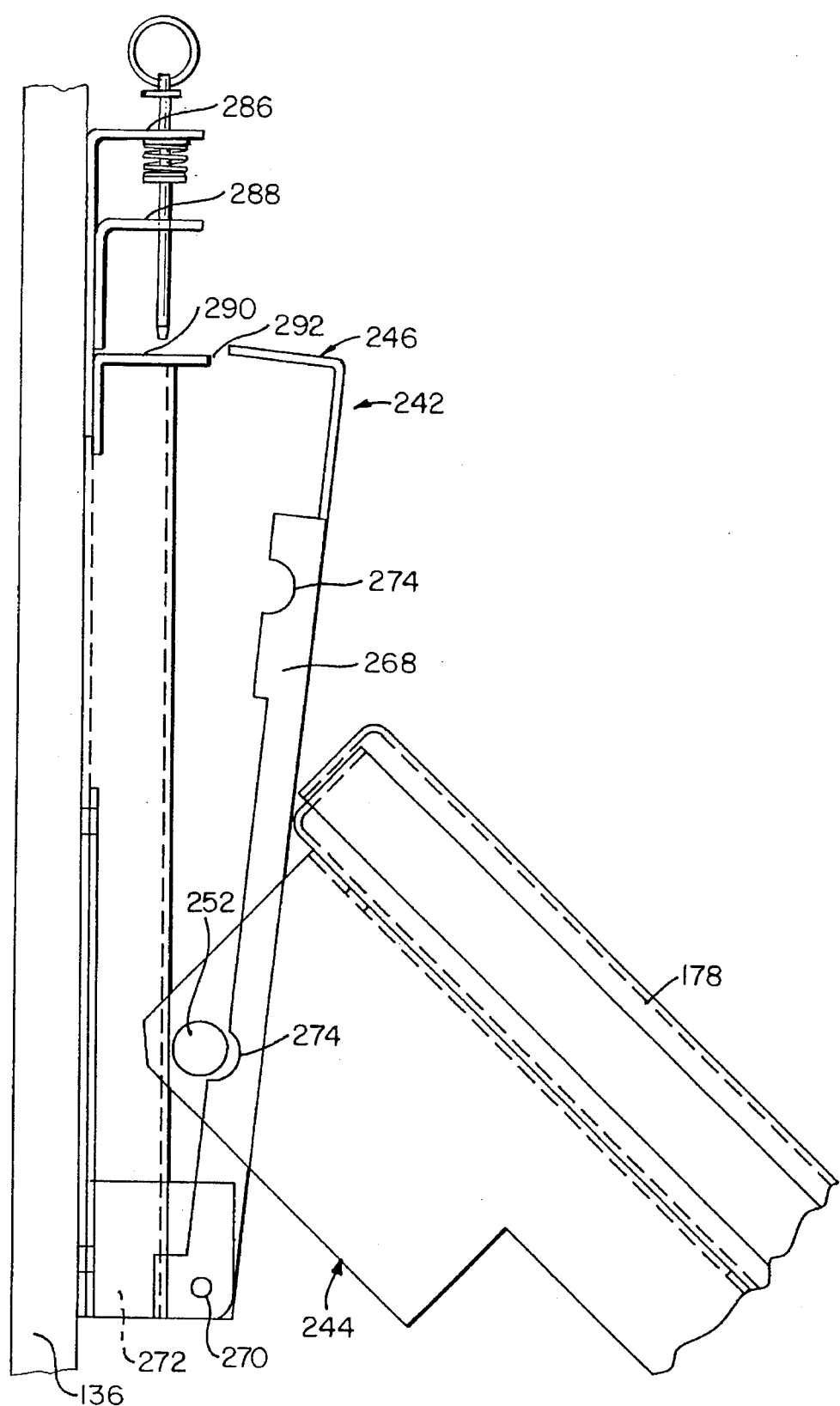
FIG. 17 is a front elevational view showing operation of the locking assembly in positioning the backrest from one position to another.
Figure 18:
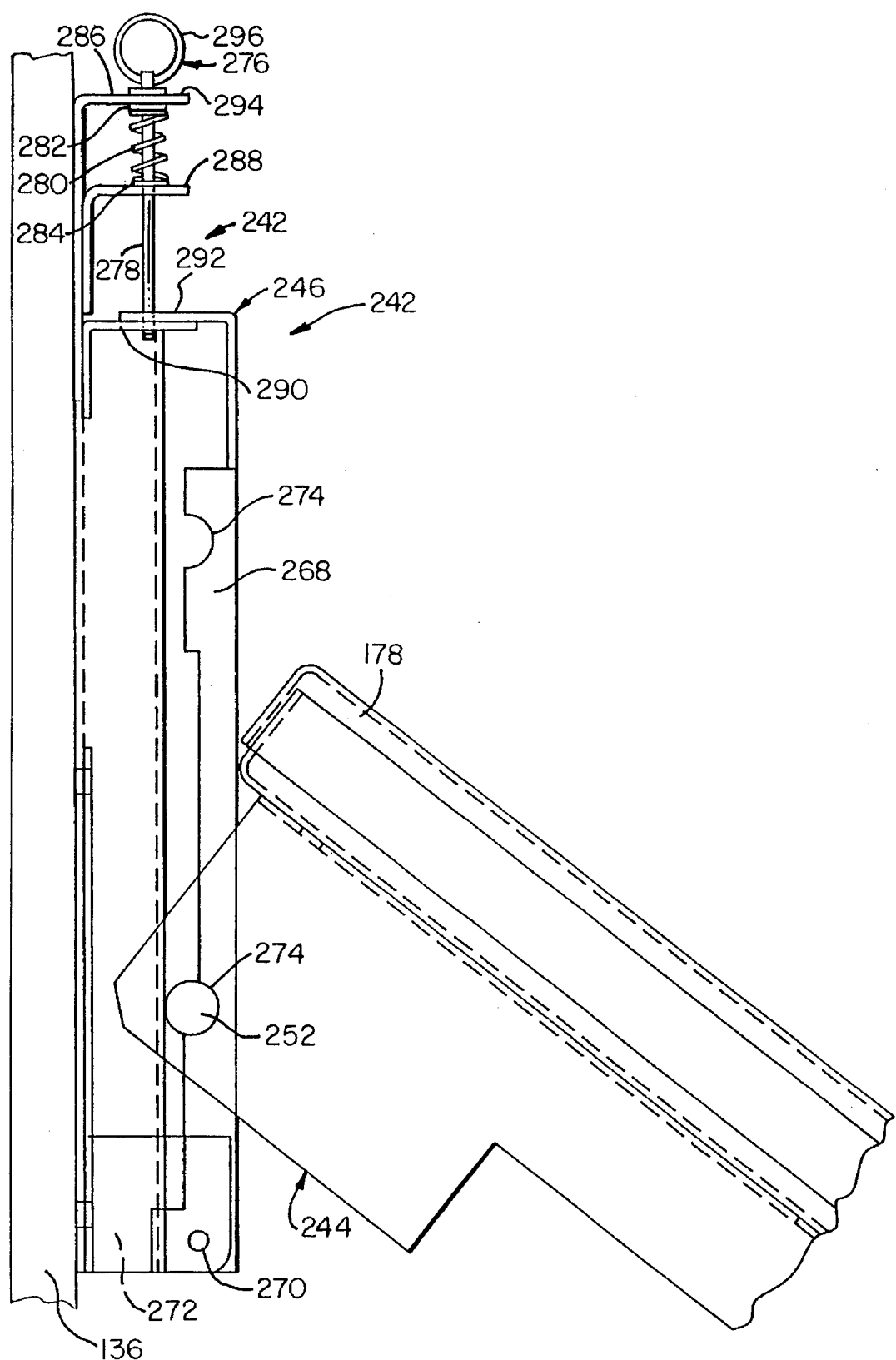
FIG. 18 is a front elevational view of the locking assembly showing the backrest releasably secured in one of a plurality of positions.

Turning now to FIGS. 15, 17 and 18, the backrest 178 is secured in a vertical position by means of rod 252 being captured within the uppermost notch 274 of the locking bar 268. In order to adjust the incline of the backrest 178, the pin assembly 276 is engaged by means of ring 296. By pulling the ring 296 upwardly, shaft 278 may be withdrawn from the aligned openings within the bracket 290 and flange 292 of the locking bar 268. Once disengaged, the locking bar 268 may be rotated about shaft 270 away from its closed position as shown in FIG. 15, to its open position as shown in FIG. 17. Once the locking bar 268 has been arranged in its open position, notch 274 releases its captured relationship of rod 252 thereby allowing the backrest 178 to reorient itself in a new angular position. In this regard, the rod 252 slides downwardly within the channel 266 as the backrest 178 moves from a vertical to an angular position.

The backrest 178 may be locked in its new position, as shown in FIG. 18, by once again capturing rod 252 in a lower notch 274 of the locking bar 268 and returning the locking bar to its closed locked position. The locking bar 268 is secured in its closed position by release of the pin assembly 276 so as to extend the shaft 278 through the aligned openings of bracket 290 and flange 292. By providing a plurality of notches 274, the backrest 178 may be oriented in a plurality of different positions as may be required by the user for comfort and/or administration of medical procedures and the like.

Although the invention herein has been described with reference to particular embodiments, it is to be understood that the embodiments are merely illustrative of the principles and application of the present invention. It is therefore to be understood that numerous modifications may be made to the embodiments and that other arrangements may be devised without departing from the spirit and scope of the present invention as defined by the claims.

What is claimed is:

1. A treatment booth for confining a person having a communicable disease in an isolated environment, said booth comprising a housing having a floor for confining a person therein, a frame supporting said floor including a plurality of elongated first members and a plurality of elongated second members arranged in a grid, said first members having a plurality of spaced apart openings for receiving said second members therein wherein the upper surface of said first members is substantially flush with the upper surface of said second members for support of said floor thereacross, said first members constructed as U-shaped members having a bottom wall, a pair of spaced apart side walls of equal height and outwardly extending flanges substantially flush with the upper surface of said second members, said flanges transversely arranged at the upper ends of said side walls for supporting said floor thereon, said openings within said first members formed from cut out portions from each of said side walls in alignment with each other and from said flanges, said openings within said side walls comprising rectangular opening and a pair of notches on either side of said rectangular opening, access means within said housing for ingress and egress of a person into and out of the interior of said housing, and treatment means within said housing for treating the contaminated environment within the interior of said housing resulting from the presence of a person therein having a communicable disease.

2. The booth of claim 1, wherein said openings within said first members have a predetermined shape, said second members having a corresponding predetermined shape in cross-section.

3. The booth of claim 1, wherein said second members are constructed as U-shaped members having a bottom wall, a pair of spaced apart solid side walls of equal height and outwardly extending flanges transversely arranged at the upper ends of said side walls.

4. The booth of claim 3, wherein said bottom wall and said side walls of said second members are received within said rectangular opening and said flanges of said second members are received within said notches.

5. The booth of claim 1, further including a seat within said housing for supporting a person thereon having a position adjustable backrest, a locking assembly for releasably locking said backrest in a plurality of positions, said locking assembly comprising a tracking guide attached to said backrest and a locking bracket releasably engaging said tracking guide for securing said backrest in said plurality of positions.

6. The booth of claim 5, wherein said tracking guide comprises a U-shaped member having a rod secured thereacross, said rod releasably engaging said locking bracket for securing said backrest in one of said plurality of positions, said locking bracket comprising an outer member, an inner member received within said outer member forming a channel therebetween receiving said rod of said tracking guide, a pivotable member overlying said channel, said pivotable member having a plurality of openings for receiving said rod for securing said backrest in one of said plurality of positions and a flange overlying a portion of said inner member, and securing means for releasably securing said flange to said portion of said inner member.

7. The booth of claim 1, wherein said treatment means comprises an air filter assembly including a primary filter for treatment of contaminated air within said housing, a first frame overlying one surface of said primary filter having an opening in communication therewith for the flow of contaminated air therethrough, a prefilter overlying said opening within said first frame, and a second frame overlying one surface of said prefilter having an opening in communication therewith for the flow of contaminated air therethrough, said second frame having a portion releasably secured by a portion of said first frame, whereby said primary filter and said prefilter are accessible for replacement upon removal of said first and second frames.

8. The booth of claim 7, wherein said second frame includes a flange arranged at an angle to said second frame for engaging a portion of said booth for releasably securing said second frame thereat.

9. The booth of claim 1, wherein said housing further includes a transom above said access means extending entirely from one end of said housing to an opposite end thereof.

10. A treatment booth for confining a person having a communicable disease in an isolated environment, said booth comprising a housing having a floor for confining a person therein, a frame supporting said floor including a plurality of elongated U-shaped longitudinal members and a plurality of elongated U-shaped transverse members arranged in a grid, said longitudinal members including a bottom wall, a pair of spaced apart solid side walls of equal height and outwardly extending flanges at the upper ends of said side walls for supporting said floor thereon, said transverse members including a bottom wall, a pair of spaced apart solid side walls of equal height and outwardly extending flanges at the upper ends of said side walls for supporting said floor thereon, said longitudinal members having a plurality of spaced apart openings for receiving said transverse members therein, said openings comprising a rectangular opening within each of said side walls in alignment with each other and a pair of notches on either side of said rectangular opening, said transverse members having said bottom wall and said side walls thereof received within said rectangular openings and said flanges received within said notches, said bottom wall of said transverse members supported by said side walls of said longitudinal members forming said rectangular openings, wherein the upper surface of said flanges of said longitudinal members is substantially flush with the upper surface of said flanges of said transverse members for support of said floor thereacross, access means within said housing for ingress and egress of a person into and out of the interior of said housing, and treatment means within said housing for treating the contaminated environment within the interior of said housing resulting from the presence of a person therein having a communicable disease.

11. A treatment booth for confining a person having a communicable disease in an isolated environment, said booth comprising a housing for confining a person therein, access means within said housing for ingress and egress of a person into and out of the interior of said housing, and an air filter assembly within said housing for treating the contaminated environment therein resulting from the presence of a person having a communicable disease, said air filter assembly comprising a primary filter for treatment of contaminated air within said housing, a first frame separate from said primary filter overlying one surface of said primary filter having an opening in communication therewith for the flow of contaminated air therethrough, a prefilter overlying said opening within said first frame, and a second frame separate from said prefilter overlying one surface of said prefilter having an opening in communication therewith for the flow of contaminated air therethrough, said second frame having a portion releasably secured by a portion of said first frame whereby said primary filter and said prefilter are accessible for replacement upon removal of said first and second frames.

12. The booth of claim 11, further including means for simultaneously securing said primary filter and said first frame overlying one another within said housing.

13. The booth of claim 11, wherein said second frame has another portion engaging a portion of said housing for releasably securing said second frame thereat.

14. The booth of claim 13, wherein said another portion of said second frame comprises a flange arranged at an angle to said second frame.

15. The booth of claim 11, wherein said portion of said first frame comprises a U-shaped member extending outwardly along one side thereof.

16. The booth of claim 11, further including means within said housing for drawing contaminated air from within said housing through both said prefilter and said primary filter, and discharging clean filtered air to the surrounding environment outside said housing, said means located adjacent said primary filter.

17. The booth of claim 11, further including a seat within said housing for supporting a person thereon having a position adjustable backrest, a locking assembly for releasably locking said backrest in a plurality of positions, said locking assembly comprising a tracking guide attached to said backrest and a locking bracket releasably engaging said tracking guide for securing said backrest in said plurality of positions.

18. The booth of claim 17, wherein said tracking guide comprises a U-shaped member having a rod secured thereacross, said rod releasably engaging said locking bracket for securing said backrest in one of said plurality of positions, said locking bracket comprising an outer member, an inner member received within said outer member forming a channel therebetween receiving said rod of said tracking guide, a pivotable member overlying said channel, said pivotable member having a plurality of openings for receiving said rod for securing said backrest in one of said plurality of positions and a flange overlying a portion of said inner member, and securing means for releasably securing said flange to said portion of said inner member.

19. The booth of claim 11, further including a frame supporting a floor within said housing, said frame including a plurality of elongated longitudinal members and a plurality of elongated transverse members arranged in a grid, said longitudinal members having a plurality of spaced apart openings for receiving said transverse members therein wherein the upper surface of said longitudinal members is substantially flush with the upper surface of said transverse members for support of said floor thereacross.

20. The booth of claim 19, wherein said openings comprise a rectangular opening and a pair of notches on either side of said rectangular opening, said transverse members having one portion received within said rectangular opening and another portion received within said notches.

21. The booth of claim 11, wherein said housing further includes a transom above said access means extending entirely from one end of said housing to an opposite end thereof.

22. A treatment booth for confining a person having a communicable disease in an isolated environment, said booth comprising a housing for confining a person therein, access means within said housing for ingress and egress of a person into and out of the interior of said housing, and an air filter assembly within said housing for treating the contaminated environment therein resulting from the presence of a person having a communicable disease, said air filter assembly comprising a primary filter for treatment of contaminated air within said housing, a first frame overlying one surface of said primary filter having an opening in communication therewith for the flow of contaminated air therethrough, a prefilter overlying said opening within said first frame, and a second frame overlying one surface of said prefilter having an opening in communication therewith for the flow of contaminated air therethrough, said second frame having one portion releasably secured by a U-shaped member extending outwardly along one side of said first frame and another portion engaging a portion of said housing for releasably securing said second frame threat, whereby said primary filter and said prefilter are accessible for replacement upon removal of said first and second frames, and means within said housing for drawing contaminated air from within said housing through both said prefilter and said primary filter, and discharging clean filtered air to the surrounding environment outside said housing.

23. A treatment booth for confining a person having a communicable disease in an isolated environment, said booth comprising a housing for confining a person therein, a seat within said housing for supporting a person having a position adjustable backrest, a locking assembly for releasably locking said backrest in a plurality of positions, said locking assembly including a tracking guide attached to said backrest and a locking bracket releasably engaging said tracking guide for securing said backrest in said plurality of positions.

24. The booth of claim 23, wherein said tracking guide comprises a U-shaped member having a rod secured thereacross, said rod releasably engaging said locking bracket for securing said backrest in one of said plurality of positions.

25. The booth of claim 24, wherein said U-shaped member includes a bottom wall and a pair of spaced apart side walls, said rod outwardly extending transversely from said side walls beyond the extent thereof.

26. The booth of claim 24, wherein said locking bracket comprises an outer member, an inner member received within said outer member forming a channel therebetween receiving said rod of said tracking guide, a pivotable member overlying said channel, said pivotable member having a plurality of openings for receiving said rod for securing said backrest in one of said plurality of positions and a flange overlying a portion of said inner member, and securing means for releasably securing said flange to said portion of said inner member.

27. The booth of claim 26, wherein said securing means comprise a spring biased pin extending through an opening within said flange aligned with an opening within said portion of said inner member.

28. The booth of claim 26, wherein said outer member and said inner member comprise U-shaped elongated members having inwardly turned flanges opposing one another to form said channel therebetween.

29. The booth of claim 23, further including a frame supporting a floor within said housing, said frame including a plurality of elongated longitudinal members and a plurality of elongated transverse members arranged in a grid, said longitudinal members having a plurality of spaced apart openings for receiving said transverse members therein wherein the upper surface of said longitudinal members is substantially flush with the upper surface of said transverse members for support of said floor thereacross.

30. The booth of claim 29, wherein said openings comprise a rectangular opening and a pair of notches on either side of said rectangular opening, said transverse members having one portion received within said rectangular opening and another portion received within said notches.

31. The booth of claim 23, further including an air filter assembly within said housing for treating the contaminated environment therein resulting from the presence of a person having a communicable disease, said air filter assembly comprising a primary filter for treatment of contaminated air within said housing, a first frame overlying one surface of said primary filter having an opening in communication therewith for the flow of contaminated air therethrough, a prefilter overlying said opening within said first frame, and a second frame overlying one surface of said prefilter having an opening in communication therewith for the flow of contaminated air therethrough, said second frame having a portion releasably secured by a portion of said first frame, whereby said primary filter and said one filter are accessible for replacement upon removal of said first and second frames.

32. The booth of claim 31, wherein said second frame includes a flange arranged at an obtuse angle to said second frame engaging a portion of said housing for releasably securing said second frame thereat.

33. The booth of claim 31, further including means within said housing for drawing contaminated air from within said housing through both said prefilter and said primary filter, and discharging clean filtered air to the surrounding environment outside said housing.

34. The booth of claim 33, further including access means within said housing for ingress and egress of a person into and out of the interior of said housing.

35. A treatment booth for confining a person having a communicable disease in an isolated environment, said booth comprising a housing for confining a person therein, a seat within said housing for supporting a person having a position adjustable backrest, a locking assembly for releasably locking said backrest in a plurality of positions, said locking assembly including a tracking guide attached to said backrest comprising a U-shaped member having a rod for securing said backrest in one of said plurality of positions, and a locking bracket releasably engaging said tracking guide for securing said backrest in said plurality of positions, said locking bracket including an outer member, an inner member received within said outer member forming a channel therebetween receiving said rod of said tracking guide, a pivotable member overlying said channel, said pivotable member having a plurality of openings for receiving said rod for securing said backrest in one of said plurality of positions and a flange overlying a portion of said inner member, and securing means for releasably securing said flange to said portion of said inner member.

36. The booth of claim 35, further including treatment means within said housing for treating the contaminated environment within the interior of said housing resulting from the presence of a person therein having a communicable disease.

37. A treatment booth for confining a person having a communicable disease in an isolated environment, said booth comprising a housing having a floor for confining a person therein; a frame supporting said floor including a plurality of elongated U-shaped longitudinal members and a plurality of elongated U-shaped transverse members arranged in a grid, said longitudinal members having a plurality of spaced apart openings for receiving said transverse members therein, said openings comprising a rectangular opening and a pair of notches on either side of said rectangular opening, said transverse members having one portion received within said rectangular opening and another portion received within said notches wherein the upper surface of said longitudinal members is substantially flush with the upper surface of said transverse members for support of said floor thereacross; access means within said housing for ingress and egress of a person into and out of the interior of said housing; a seat within said housing for supporting a person having a position adjustable backrest; a locking assembly for releasably locking said backrest in a plurality of positions, said locking assembly including a tracking guide attached to said backrest comprising a U-shaped member having a rod for securing said backrest in one of said plurality of positions, and a locking bracket releasably engaging said tracking guide for securing said backrest in said plurality of positions, said locking bracket including an outer member, an inner member received within said outer member forming a channel therebetween receiving said rod of said tracking guide, a pivotable member overlying said channel, said pivotable member having a plurality of openings for receiving said rod for securing said backrest in one of said plurality of positions and a flange overlying a portion of said inner member, and securing means for releasably securing said flange to said portion of said inner member; treatment means within said housing for treating the contaminated environment within the interior of said housing resulting from the presence of a person therein having a communicable disease, said treatment means comprising a primary filter for treatment of contaminated air within said housing, a first frame overlying one surface of said primary filter having an opening in communication therewith for the flow of contaminated air therethrough, a prefilter overlying said opening within said first frame, and a second frame overlying one surface of said prefilter having an opening in communication therewith for the flow of contaminated air therethrough, said second frame having one portion releasably secured by a U-shaped member extending outwardly along one side of said first frame and another portion engaging a portion of said housing for releasably securing said second frame threat, whereby said primary filter and said prefilter are accessible for replacement upon removal of said first and second frames; and means within said housing for drawing contaminated air from within said housing through both said prefilter and said primary filter and discharging clean filtered air to the surrounding environment outside said housing.

38. A treatment booth for confining a person having a communicable disease in an isolated environment, said booth comprising a housing having a floor for confining a person therein, a frame supporting said floor including a plurality of elongated first members and a plurality of elongated second members arranged in a grid, said first members having a plurality of spaced apart openings for receiving said second members therein wherein the upper surface of said first members is substantially flush with the upper surface of said second members for support of said floor thereacross, access means within said housing for ingress and egress of a person into and out of the interior of said housing, a seat within said housing for supporting a person thereon having a position adjustable backrest, a locking assembly for releasably locking said backrest in a plurality of positions, said locking assembly comprising a tracking guide attached to said backrest and a locking bracket releasably engaging said tracking guide for securing said backrest in said plurality of positions, and treatment means within said housing for treating the contaminated environment within the interior of said housing resulting from the presence of a person therein having a communicable disease.

39. A treatment booth for confining a person having a communicable disease in an isolated environment, said booth comprising a housing having a floor for confining a person therein, a frame supporting said floor including a plurality of elongated first members and a plurality of elongated second members arranged in a grid, said first members having a plurality of spaced apart openings for receiving said second members therein wherein the upper surface of said first members is substantially flush with the upper surface of said second members for support of said floor thereacross, access means within said housing for ingress and egress of a person into and out of the interior of said housing, and treatment means within said housing for treating the contaminated environment within the interior of said housing resulting from the presence of a person therein having a communicable disease, said treatment means comprising an air filter assembly including a primary filter for treatment of contaminated air within said housing, a first frame overlying one surface of said primary filter having an opening in communication therewith for the flow of contaminated air therethrough, a prefilter overlying said opening within said first frame, and a second frame overlying one surface of said prefilter having an opening in communication therewith for the flow of contaminated air therethrough, said second frame having a portion releasably secured by a portion of said first frame, said second frame including a flange arranged at an angle to said second frame for engaging a portion of said booth for releasably securing said second frame thereat, whereby said primary filter and said prefilter are accessible for replacement upon removal of said first and second frames.

40. A treatment booth for confining a person having a communicable disease in an isolated environment, said booth comprising a housing for confining a person therein, access means within said housing for ingress and egress of a person into and out of the interior of said housing, an air filter assembly within said housing for treating the contaminated environment therein resulting from the presence of a person having a communicable disease, said air filter assembly comprising a primary filter for treatment of contaminated air within said housing, a first frame overlying one surface of said primary filter having an opening in communication therewith for the flow of contaminated air therethrough, a prefilter overlying said opening within said first frame, and a second frame overlying one surface of said prefilter having an opening in communication therewith for the flow of contaminated air therethrough, said second frame having a portion releasably secured by a portion of said first frame whereby said primary filter and said prefilter are accessible for replacement upon removal of said first and second frames, and a seat within said housing for supporting a person thereon having a position adjustable backrest, a locking assembly for releasably locking said backrest in a plurality of positions, said locking assembly comprising a tracking guide attached to said backrest and a locking bracket releasably engaging said tracking guide for securing said backrest in said plurality of positions.

41. A treatment booth for confining a person having a communicable disease in an isolated environment, said booth comprising a housing for confining a person therein, access means within said housing for ingress and egress of a person into and out of the interior of said housing, and an air filter assembly within said housing for treating the contaminated environment therein resulting from the presence of a person having a communicable disease, said air filter assembly comprising a primary filter for treatment of contaminated air within said housing, a first frame overlying one surface of said primary filter having an opening in communication therewith for the flow of contaminated air therethrough, a prefilter overlying said opening within said first frame, and a second frame overlying one surface of said prefilter having an opening in communication therewith for the flow of contaminated air therethrough, said second frame having a portion releasably secured by a portion of said first frame whereby said primary filter and said prefilter are accessible for replacement upon removal of said first and second frames, said second frame having another portion engaging a portion of said housing for releasably securing said second frame thereat.

42. A treatment booth for confining a person having a communicable disease in an isolated environment, said booth comprising a housing for confining a person therein, access means within said housing for ingress and egress of a person into and out of the interior of said housing, and an air filter assembly within said housing for treating the contaminated environment therein resulting from the presence of a person having a communicable disease, said air filter assembly comprising a primary filter for treatment of contaminated air within said housing, a first frame overlying one surface of said primary filter having an opening in communication therewith for the flow of contaminated air therethrough, a prefilter overlying said opening within said first frame, and a second frame overlying one surface of said prefilter having an opening in communication therewith for the flow of contaminated air therethrough, said second frame having a portion releasably secured by a portion of said first frame whereby said primary filter and said prefilter are accessible for replacement upon removal of said first and second frames, said portion of said first frame comprising a U-shaped member extending outwardly along one side thereof.

* * * * *

UNITED STATES PATENT AND TRADEMARK OFFICE
CERTIFICATE OF CORRECTION

PATENT NO. : 5,533,305

DATED : July 9, 1996

INVENTOR(S) : James J. Bielecki

It is certified that error appears in the above-identified patent and that said Letters Patent is hereby corrected as shown below:

On the title page:
Attorney, Agent, or Firm, "Lerner, David, Littenberg" should read --Lerner, David, Littenberg, Krumholz & Mentlik--.

Signed and Sealed this

Twenty-second Day of October, 1996

Attest:

BRUCE LEHMAN

Attesting Officer     Commissioner of Patents and Trademarks